US00PP13236P3

(12) United States Plant Patent
Geenty

(10) Patent No.: US PP13,236 P3
(45) Date of Patent: Nov. 19, 2002

(54) AGAPANTHUS PLANT NAMED 'SARAH'

(76) Inventor: Mike Geenty, 103 Memorial Drive, Hamilton (NZ)

( * ) Notice: Subject to any disclaimer, the term of this patent is extended or adjusted under 35 U.S.C. 154(b) by 145 days.

(21) Appl. No.: 09/760,914

(22) Filed: Jan. 16, 2001

(65) Prior Publication Data

US 2002/0095702 P1 Jul. 18, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct *Agapanthus praecox* plant named 'Sarah' characterized by its distinctly arranged upward pointing florets producing a candelabra shaped umbel, bicolored florets and dark green foliage.

4 Drawing Sheets

LATIN NAME OF THE GENUS AND SPECIES OF PLANT CLAIMED

*Agapanthus praecox* 'Sarah'.

BACKGROUND OF THE INVENTION

The present invention comprises a new and distinct Agapanthus plant, hereinafter referred to by the cultivar name 'Sarah'. This new cultivar was developed by the inventor through a controlled breeding program during 1993 in Hamilton, New Zealand.

The female parent of 'Sarah' was an unnamed *Agapanthus praecox* seedling which is characterized by its strong stem, blue to lilac flower color and leaf color atypical for *praecox* species. The male parent of 'Sarah' was a proprietary *Agapanthus praecox* seedling which is characterized by its profuse florets and leaf color atypical for *praecox* species. The resulting seed was collected and germinated. From the flowering progeny, a plant was selected in 1996 and initially designated Agapanthus 007.

Asexual reproduction of the new cultivar by divisions taken in New Zealand has demonstrated that the characteristics of the new cultivar as herein described are firmly fixed and are retained through successive generations of such asexual propagation.

SUMMARY OF THE INVENTION

The following traits have been repeatedly observed and are determined to be the unique characteristics of 'Sarah'. These characteristics in combination distinguish 'Sarah' as a new and distinct cultivar.

It was found that the cultivar of the present invention:

(a) Exhibits a unique candelabra shaped umbel;

(b) Forms bi-colored purple flowers; and (c) Exhibits dense dark green foliage.

When the new cultivar of the present invention is compared to 'Peter Pan' (non-patented) it is found that the new cultivar exhibits a distinctly different inflorescence which is candelabra shaped.

BRIEF DESCRIPTION OF THE PHOTOGRAPHS

The accompanying photographs show as nearly true as it is reasonably possible to make the same in color illustrations of this type, typical flower and foliage characteristics of the new cultivar.

DETAILED BOTANICAL DESCRIPTION

Figure 1A:
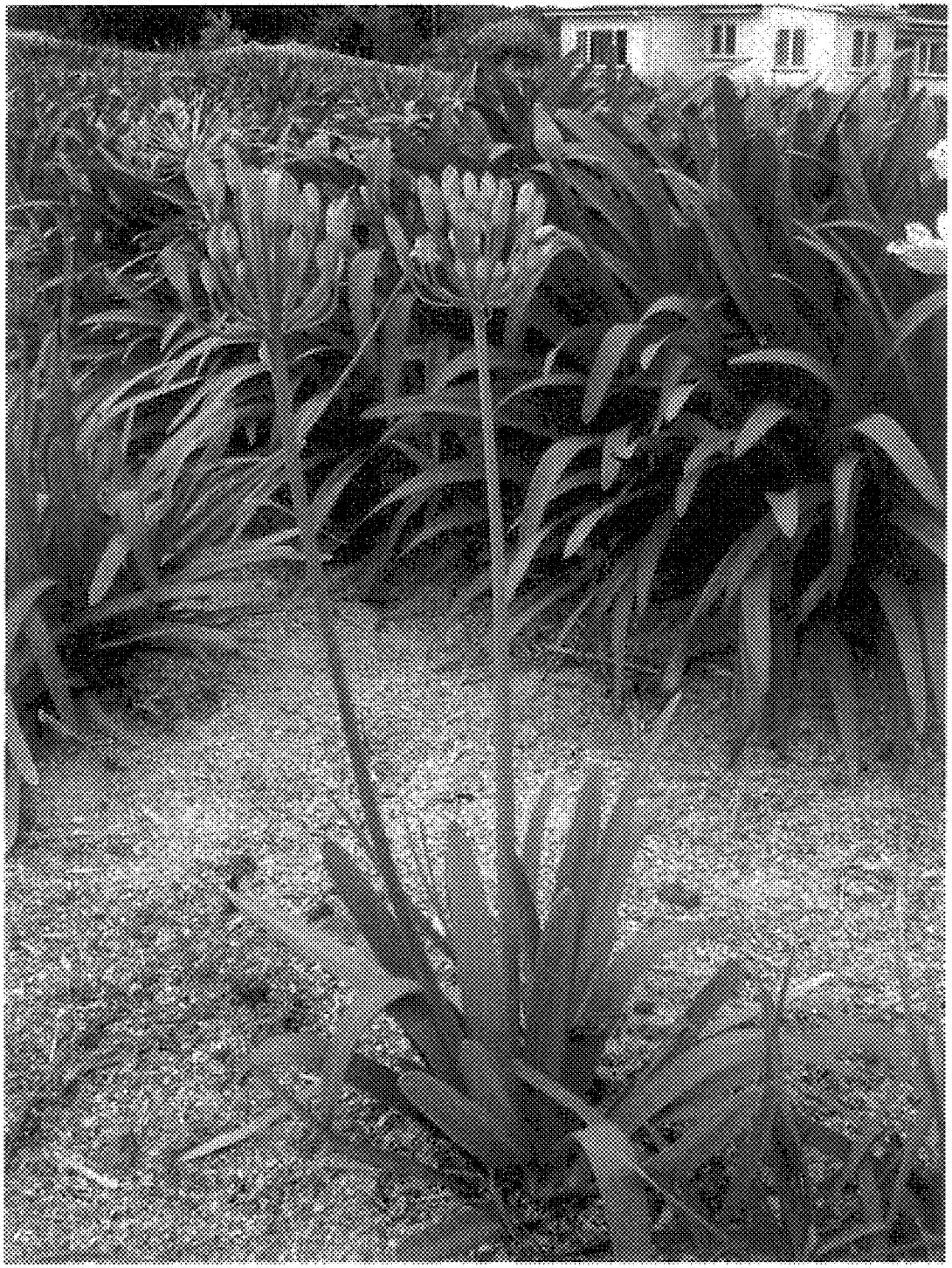
FIG. 1A shows the whole plant with umbels in bud.
Figure 1B:
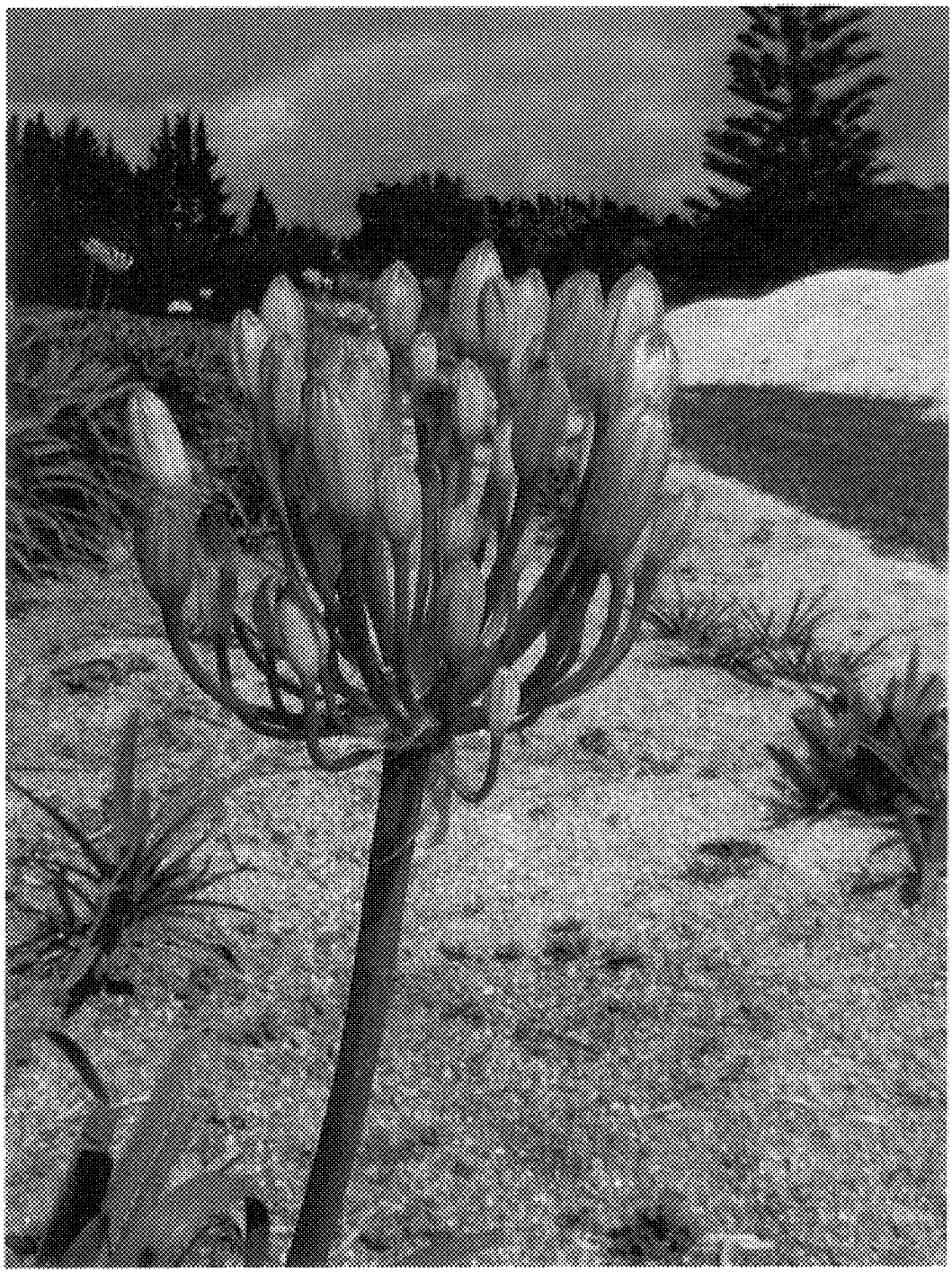
FIG. 1B shows a close up of a single umbel.
Figure 1C:
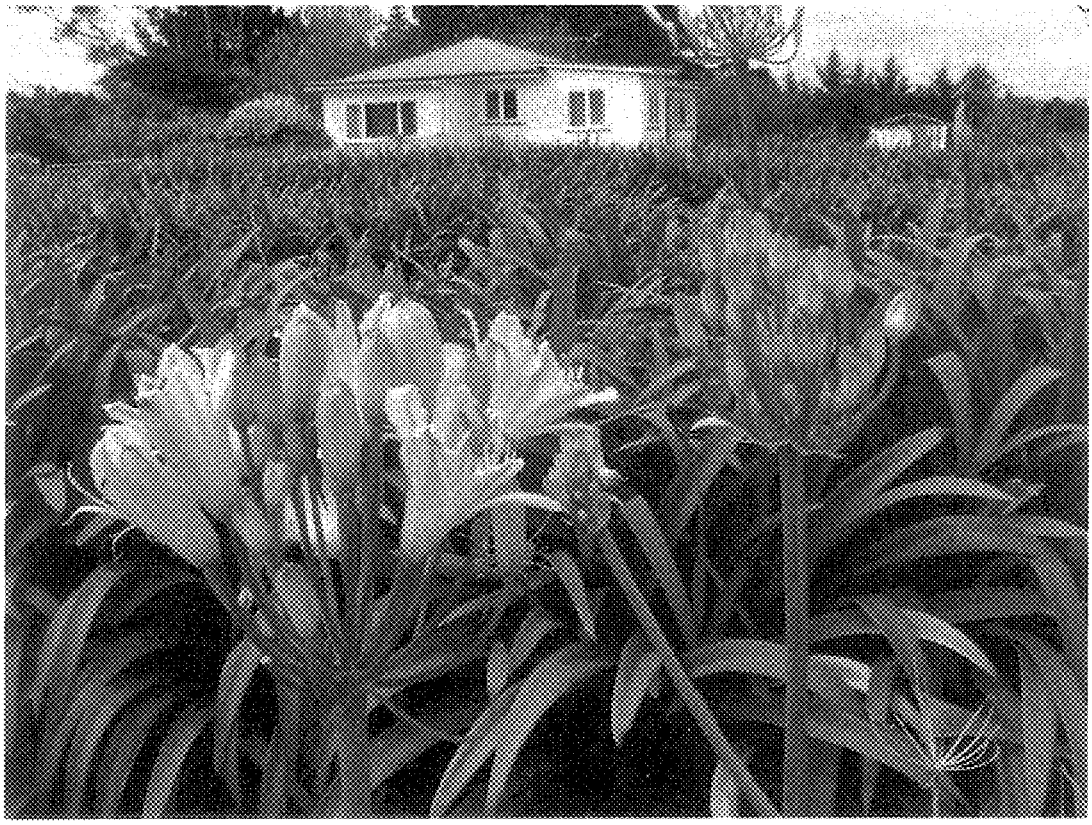
FIG. 1C shows a typical umbel.
Figure 1D:
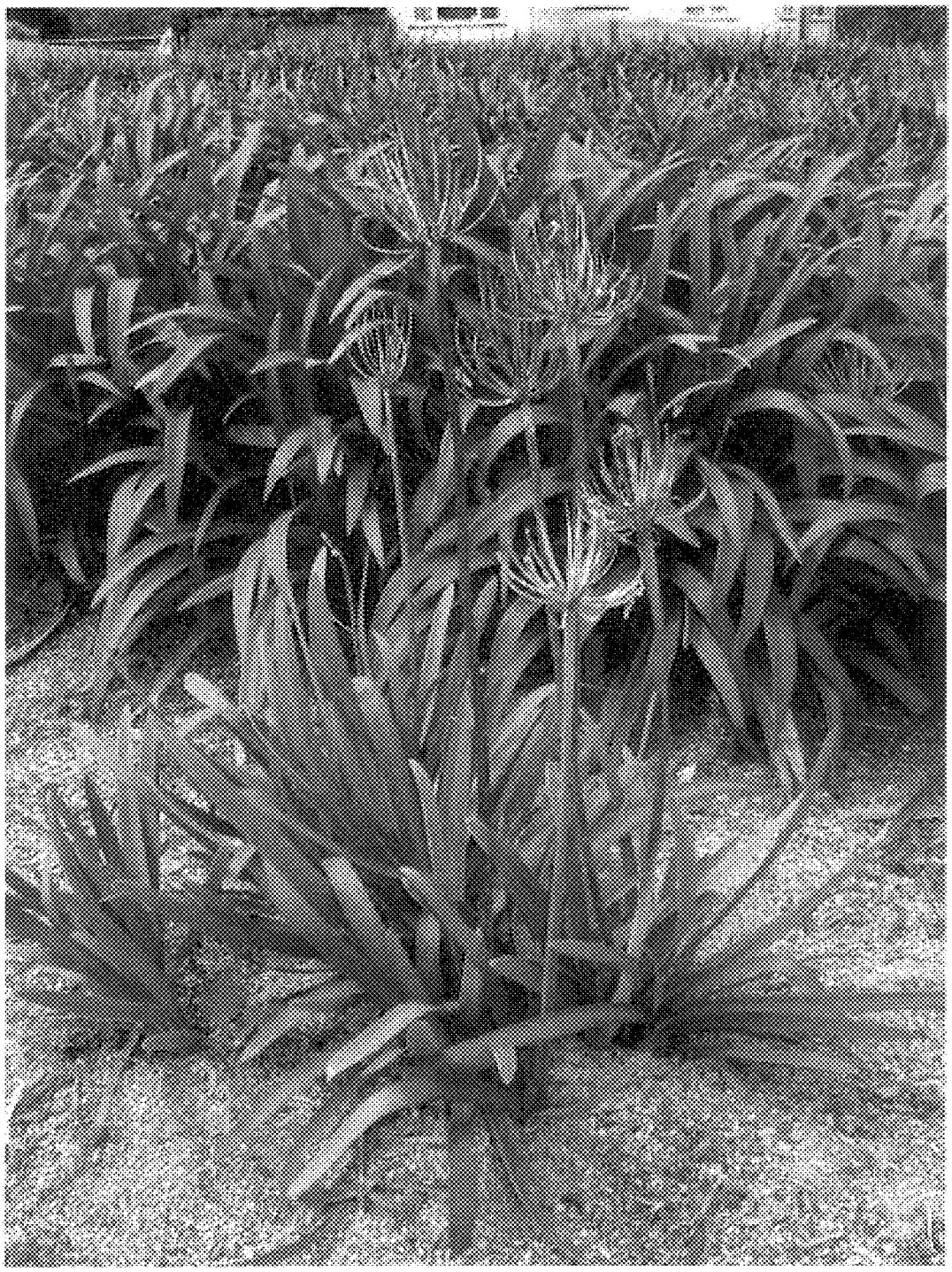
FIG. 1D shows plants having umbels, after senescence, with no seed formation.

The 'Sarah' cultivar has not been observed under all possible environmental conditions to date. Accordingly, it is possible that the phenotype may vary somewhat with variations in the environment, such as temperature, light intensity and day length.

The chart used in the identification of colors described herein is The R.H.S. Colour Chart of The Royal Horticultural Society, London, England. The plants were produced from divisions taken from stock plants and were grown for two years in Hamilton, New Zealand.

Classification:
- *Botanical.*—*Agapanthus praecox* cultivar 'Sarah'.
- *Commercial.*—Agapanthus.

Propagation:
- *Type.*—Division.
- *Time to initiate roots.*—Approximately 30 days.
- *Rooting habit.*—Prolific.

Plant description:
- *General appearance and form.*—Evergreen perennial herb with dense, dark green foliage without variegation.
- *Rhizome.*—Fleshy tuberous.
- *Plant height.*—Approximately 40–60 cm.
- *Plant spread.*—Approximately 30–40 cm.
- *Scapes.*—Rigid; Length 55–70 cm; Diameter approximately 8 mm.

Foliage description:

*General description and form.*—Leaves are distichously arranged arising from near the ground and united into a stout pseudo-bulb, glabrous and canaliculate towards the base from the center.

*Texture.*—Thin, glaucous.

*Shape.*—Ligulate-lorate, with entire margin, acute/rounded apex and sessile base.

*Color of mature foliage.*—Upper surface, RHS Green Group 138B; lower surface, RHS Green Group 138C.

*Size of mature leaves.*—Aproximately 45–60 cm in length; approximately 1.5–2 cm in width.

Inflorescence description:

*General appearance and form.*—Outer whorl of pedicels arising from a scape at right angles and then curving to eventuate in a vertical position to form an almost symmetrical un-congested, candelabra shaped umbel.

*Umbel size.*—14 cm high, 15 cm wide.

*Bracts.*—Subtended by the florets. Arising from the junction of the pedicel and scape; 4 mm long, papery and persistent.

*Flowering habit.*—'Sarah' is freely flowering under outdoor growing conditions with substantially continuous blooming from spring until fall.

Flower description:

*General description and appearance.*—Very numerous, actinomorphic with canaliculate tepals, epipetalous stamens, open mouthed and upward facing.

*Flower longevity.*—Approximately 30 days.

*Quantity of flowers.*—50–60 florets per umbel.

*Umbel size.*—14 cm high, 15 cm wide.

*Bracts.*—Color of the bracts is closest to 137C.

*Floret size.*—Length; approximately 3.5 cm; width: approximately 4 cm.

*Floret color.*—RHS Violet-Blue Group 92D with a 3 mm broad, prominent central band of darker pigmentation of RHS Violet-Blue Group 92B present from the apex of the tepal to the position where they become connate. Tepal margins are RHS Violet-Blue Group 92C. Florets fading to RHS Purple-Violet Group 80B. Outer base of corolla tube where it joins the pedicel is RHS Green Group 143C, suffusing in some cases 1 cm along abaxial surface of the tepal.

*Tepals.*—Margins noticeably undulate on the broader tepals and not overlapping. Tepals conspicuously canaliculate. Number — 9–12; length — 3.7 cm from where it joins the pedicel.

*Pedicels.*—Outer whorl 7.5 cm long; inner whorl 9.5 cm long.

*Reproductive organs.*—Androecium: prominent and exerted with adnate filaments and dorsifixed and versatile anther lobes. Stamens: number — 9; length — 3 cm. Pollen color is yellow, maturing to orange brown with anther maturing to dark brown before withering. Gynoecium — one pistil, 2.8 cm long. Stigma: 2 cm in length. Occasionally 4–5 stigmas present from a single floret. Ovary: Ribbed. RHS Yellow-Green Group 144C.

*Fruits.*—Sterile.

*Seed production.*—No seed production has been observed.

I claim:

1. A new and distinct *Agapanthus praecox* plant named 'Sarah' substantially as herein shown and described, which:

(a) exhibits a unique candelabra shaped umbel;

(b) forms bi-colored purple flowers; and (c) exhibits dense dark green foliage.

* * * * *